(12) United States Patent
Sealfon et al.

(10) Patent No.: US 10,183,124 B2
(45) Date of Patent: Jan. 22, 2019

(54) SYSTEM AND METHOD FOR ERGONOMIC NEEDLE PROTECTOR

(71) Applicant: REPRO-MED SYSTEMS, INC., Chester, NY (US)

(72) Inventors: Andrew I. Sealfon, Monroe, NY (US); Siavash Gheshmi, Chester, NY (US)

( * ) Notice: Subject to any disclaimer, the term of this patent is extended or adjusted under 35 U.S.C. 154(b) by 238 days.

(21) Appl. No.: 15/291,913

(22) Filed: Oct. 12, 2016

(65) Prior Publication Data

US 2018/0099101 A1    Apr. 12, 2018

(51) Int. Cl.
*A61M 5/32*    (2006.01)
*A61M 5/158*    (2006.01)

(52) U.S. Cl.
CPC .......... *A61M 5/3245* (2013.01); *A61M 5/158* (2013.01); *A61M 5/3273* (2013.01); *A61M 2005/3246* (2013.01); *A61M 2005/3254* (2013.01)

(58) Field of Classification Search
CPC .. A61M 2005/3246; A61M 2005/3254; A61M 5/158; A61M 5/3245; A61M 5/3273; A61M 5/3202; A61M 2005/3267; A61M 2005/3284
See application file for complete search history.

(56) References Cited

U.S. PATENT DOCUMENTS

| 5,066,279 | A | * | 11/1991 | Russell | ............ | A61M 5/3213 |
|---|---|---|---|---|---|---|
| | | | | | | 604/110 |
| 5,295,963 | A | | 3/1994 | Deeks | | |
| 5,562,636 | A | | 10/1996 | Utterberg | | |
| 5,562,637 | A | | 10/1996 | Utterberg | | |
| 6,595,965 | B1 | | 6/2003 | Utterberg | | |
| 6,585,704 | B2 | | 7/2003 | Luther et al. | | |
| 7,326,189 | B2 | | 2/2008 | Mori | | |
| 2001/0056259 | A1 | | 12/2001 | Skinkle et al. | | |

(Continued)

FOREIGN PATENT DOCUMENTS

EP    1 232 763    8/2002

OTHER PUBLICATIONS

PCT International Search Report for International Application PCT/US2016/058073, search report dated Jul. 10, 2017 (Jul. 10, 2017).

(Continued)

*Primary Examiner* — Imani Hayman
(74) *Attorney, Agent, or Firm* — Daniel W. Roberts; Law Offices of Daniel W. Roberts, LLC (57) ABSTRACT

Provided is a system and method for an ergonomic needle protector. More specifically, provided is an ergonomic needle protector for a needle having a first curvature. The ergonomic needle protector has a flexible body having a first end and a second end, and an internal channel extending from the first end towards the second end. The flexible body is formed of a resilient material structured and arranged to return to a curved state along the length of the flexible body according to a second curvature different from the first curvature of the needle. The internal channel is structured and arranged to receive the needle when the flexible body is deformed to conform the internal channel to the first curvature and frictionally bind against the needle when the flexible body is released back to the second curvature. An associated method of use is also provided.

55 Claims, 6 Drawing Sheets

(56) References Cited

U.S. PATENT DOCUMENTS

| | | |
|---|---|---|
| 2005/0038399 A1 | 2/2005 | Suzuki et al. |
| 2009/0036868 A1 | 2/2009 | Pinedjian et al. |
| 2009/0240210 A1 | 9/2009 | Walton et al. |
| 2011/0087173 A1 | 4/2011 | Sibbitt, Jr. et al. |
| 2014/0221939 A1 | 8/2014 | Woehr et al. |

OTHER PUBLICATIONS

PCT International Search Report for International Application PCT/US2016/058400, search report dated Feb. 16, 2017 (Feb. 16, 2017).

\* cited by examiner

SYSTEM AND METHOD FOR ERGONOMIC NEEDLE PROTECTOR

FIELD OF THE INVENTION

The present invention relates generally to medical devices, and more specifically to systems and methods of covering and protecting a needle for safe handling and maintaining the sterile state of the needle, until such time as use of the needle is desired.

BACKGROUND

For the administration of liquid medications to patients, the use of needles is widespread and commonplace. Indeed the use of needles can be traced back to the $17^{th}$ century when Christopher Wren performed experiments using goose quills as crude hypodermic needles to deliver intravenous injections to dogs in 1656.

Dr. Alexander Wood developed an all glass syringe in 1851, thus permitting the user to estimate dosage based on observing the amount of liquid through the glass as the liquid was injected by a needle into a patient. This development by Dr. Woods significantly advanced the acceptance of injection as a medical technique.

Advancements in metallurgy permitted the manufacturing of needles of consistently specific sizes and bores and aided in 1920's growth acceptance of injecting insulin as treatment for diabetes. Disposable needles and injection systems were further developed in both World War II and the Korean War, but in the main needles themselves have remained largely unchanged.

And so too have the issues of needle care and protection. More specifically, as the needle is intended to breach the skin of a person or subject, the tip of the needle is very sharp. As the needle is often inserted below the dermis layer of the skin, the shaft of the needle can be long—ranging from a few millimeters to perhaps several inches. The shaft of the needle is also typically quite stiff so as not to bend or deflect as it is passed into the tissue of the patient. And as the needle is a foreign object being disposed into the tissues of the patient, it is very important that the needle be clean and sterile so as not to introduce foreign matter or pathogens into the patient.

Moreover, two fundamental tenants apply to needles prior to use—the needle must be protected so as to not inadvertently harm a person handling the needle, an occurrence called a needle stick, and the needle must be kept clean and sterile.

In general there are two types of needle protectors, those that fit loosely over the needle and have a coupling mechanism to engage the base of the needle and those that fit tightly over the needle itself. Forming a coupling mechanism, such as a snap connector often requires additional tooling and fabrication efforts for the both the needle base and the needle protector. In addition, if jarred loose such as by jostling during shipment or handling the protector will fall entirely off thus exposing the needle.

In many instances, such as large scale operations providing needles and needle based infusion sets for infusion therapy, the use of tight fitting straight protectors is common. These needle protectors are typically provided by an extrusion process and are intended to have nearly the same internal diameter as the outside diameter of the needle upon which they are to be used. As such, these tight fitting needle protectors remain in place due to friction between the needle and the needle protector.

Because these needle protectors are typically manufactured by an extrusion process, issues with that process, i.e. the rate of extrusion, can easily result in needle protectors that are too tight or too loose. If the needle protectors are they are too loose, some or all will fall off and thus expose the needle.

If the needle protectors are too tight, during their installation process the needle may shave off bits of the protector and become partially clogged, and thus have a diminished flow rate. This shaving or scraping of the needle protector may also occur with properly sized needle protectors if they are not installed properly.

If shaving occurs and is discovered, this may require some or all of a production run of needles to be scrapped or redone—an issue of both cost and expense to the provider, and potential delay to the end user. Even if the problem is detected, there is always the possibility that a new batch of needle protectors could suffer from the same production issue and be too tight.

In addition, due to the tight fit between the needle protector and the needle some end users who suffer from reduced dexterity and/or hand strength may have significant difficulty at times in removing the needle protector so as to use the needle.

Hence there is a need for a needle protector that overcomes one or more of the above identified challenges.

SUMMARY OF THE INVENTION

Our invention solves the problems of the prior art by providing novel systems and methods for an ergonomic needle protector.

In particular, and by way of example only, according to one embodiment of the present invention, provided is an ergonomic needle protector for a needle having a first curvature, including: a flexible body having a first end and a second end, and an internal channel extending from the first end towards the second end; the flexible body formed of a resilient material structured and arranged to return to a curved state along the length of the flexible body according to a second curvature different from the first curvature of the needle; and the internal channel structured and arranged to receive the needle when the flexible body is deformed to conform the internal channel to the first curvature and frictionally bind against the needle having the first curvature, when the flexible body is released back to the second curvature.

For yet another embodiment, provided is an ergonomic needle protector for a straight needle, including: a curved flexible body having a first end and a second end, and an internal channel extending from the first end towards the second end along the curve of the flexible body in an initial curved state; the internal channel structured and arranged to receive the straight needle when the flexible body is deformed to straighten the internal channel and frictionally bind against the straight needle when the flexible body is released back to the initial curved state.

Yet for another embodiment, provided is an infusion set with ergonomic needle protector, including: a needle having a base attached to infusion tubing, the needle having a shaft and a sharpened tip, the shaft having a first curvature; and an ergonomic needle protector having a flexible body having a first end and a second end, and an internal channel extending from the first end towards the second end along, the flexible body formed of a resilient material biased to return to a second curvature different from the first curvature, the internal channel disposed about the shaft and sharpened tip of the needle, the bias of the flexible body providing a friction hold against the shaft, wherein the ergonomic needle protector is removed by pulling it off.

For still yet another embodiment, provided is a method for protecting a needle having a first curvature with an ergonomic needle protector, including: obtaining an ergonomic needle protector having a flexible body having a first end and a second end, and an internal channel extending from the first end towards the second end, the flexible body formed of a resilient material biased to return to a second curvature different from the first curvature; flexing the flexible body in opposition to second curvature to align the internal channel to the needle; passing the internal channel loosely over the needle; and releasing the flexible body, the bias of the flexible body to the second curvature providing a friction hold against the needle.

DETAILED DESCRIPTION

Before proceeding with the detailed description, it is to be appreciated that the present teaching is by way of example only, not by limitation. The concepts herein are not limited to use or application with a specific system or method for an ergonomic needle protector. Thus although the instrumentalities described herein are for the convenience of explanation shown and described with respect to exemplary embodiments, it will be understood and appreciated that the principles herein may be applied equally in other types of systems and methods involving ergonomic needle protectors.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Figure 1:
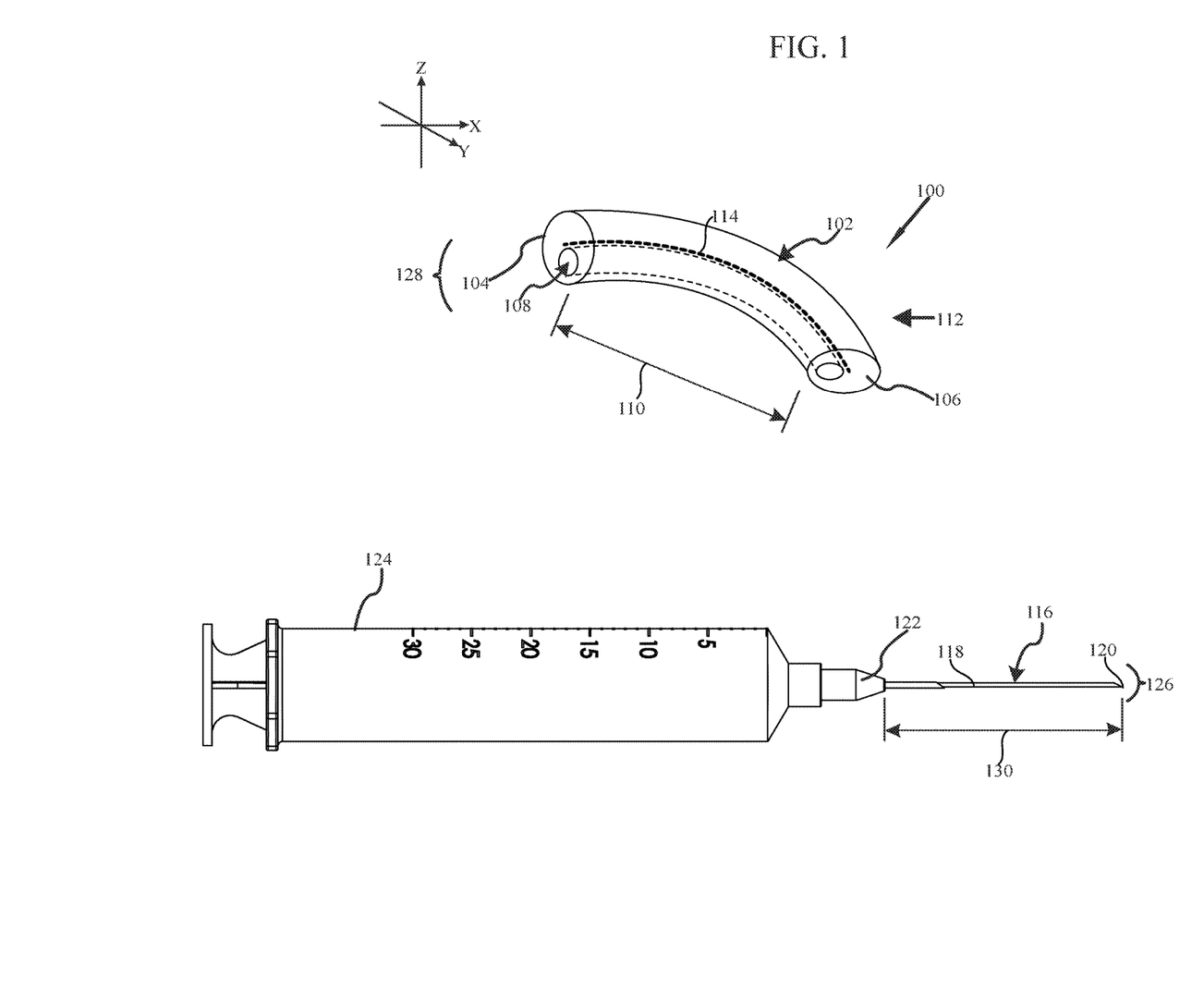
FIG. 1 is perspective illustration of an ergonomic needle protector in accordance with at least one embodiment.

Turning now to FIG. 1, there is shown an ergonomic needle protector 100, hereinafter ENP 100, in accordance with at least one embodiment of the present invention.

To facilitate the description of systems and methods for this ENP 100, the orientation of ENP 100, as presented in the figures, is referenced to the coordinate system with three axes orthogonal to one another as shown in FIG. 1. The axes intersect mutually at the origin of the coordinate system, which is chosen to be the center of ENP 100, however the axes shown in all figures are offset from their actual locations for clarity and ease of illustration.

As shown, the ENP 100 has a curved flexible body 102 having a first end 104 and a second end 106 and an internal channel 108 extending from the first end 104 towards the second end 106, and generally along the length 110 of the flexible body 102. As is clearly apparent in FIG. 1, ENP 100 is curved in its relaxed initial state due to the flexible body 102 being formed from a resilient material, such as but not limited to elastic polypropylene, hard-elastic or springy polypropylene. As such, the internal channel 108 is also curved when ENP 100 is in its relaxed initial state. This initial curved state may also be described as a first curved state 112.

For at least one embodiment, the flexible body 102 has a generally round cross section, as is apparent with respect to both the first end 104 and the second end 106. In addition, the internal channel 108 may also have a generally round cross section. Further, for at least one embodiment as shown, the internal channel 108 is offset from the longitudinal centerline 114 of the flexible body 102, such that the internal channel 108 is not concentric about the longitudinal centerline 114.

As is shown in FIG. 1, for at least one embodiment the internal channel 108 extends entirely through the flexible body 102 from the first end 104 to second end 106. For other embodiments, not shown in FIG. 1, the second end 106 may be solid or otherwise sealed such that the internal channel 108 is not exposed at the second end 106. Moreover, it is to be understood and appreciated that for some embodiments, during fabrication the internal channel 108 may initially extend entirely through the flexible body, but the second end 106 is closed, such as by crimping, gluing, melting, capping, plugging or other such sealing process as may be deemed appropriate.

Also shown in FIG. 1 is a needle 116 having a shaft 118, a sharp tip 120 and a base 122. Typically the base 122 is structured as a luer connector such that the needle 116 may be joined affixed to a syringe 124. Of course, needle 116 may also be affixed to an infusion system and/or medical tubing, but for the purposes of ease of illustration and discussion a syringe 124 has been shown.

For ease of illustration and discussion, the needle 116 has been illustrated as a typical needle affixed to a traditional syringe. With respect to the present invention, the needle is understood and appreciated to be the device or portion of the device intended to be disposed into the tissues of a patient. As such, whether the needle is curved or straight is an issue relevant to the portion to be disposed within the patient, a curve or bend in the portion that remains outside the patient being irrelevant. In other words, the "needle" is understood and appreciated to be the device that should be covered by a removable needle protector for transport and storage, and removed so that the needle may be disposed into the tissues of a patient.

It is understood and appreciated that changing what the needle 116 is attached to does not alter scope and purpose of the ENP 100. Indeed, the needle 116 may be entirely unattached with ENP 100 still serving to protect the needle 116.

With respect to FIG. 1, it is to be appreciated that the needle 116 is a straight needle. Intuitively, curvature is the amount by which a physical object deviates from being flat, as with a plane, or straight as with a line. Radius of curvature, R, is understood and appreciated to be the radius of the circular arc that best approximates the curve at a specified point. Indeed, a line having a curvature of zero "0" or radius of curvature of "0" is understood to be straight. While different metrics or context may define curvature in a wide variety of forms, for the purposes of this application it is to be understood and appreciated that needle 116 has a first curvature 126, such as zero, and ENP 100 has a second curvature 128 in the relaxed initial first curved state 112 that is different from the first curvature 126 of the needle 116. For the illustration of ENP 100 as shown in FIG. 1 this second curvature 128 is about 65°.

Moreover, in varying embodiments the curvature of ENP 100, i.e., the second curvature 128 is section of a circle, a section of an ellipse, a section of a wave form with at least one peak and one trough, and/or combinations thereof. Similarly, in varying embodiments the curvature of the needle 116 is effectively zero and thus effectively a straight needle, a section of a circle, a section of an ellipse, and/or combinations thereof.

It is to be expressly understood and appreciated that the first curvature 126 of the needle 116 and the second curvature 128 of the ENP 100 are different. As the first curvature 126 and the second curvature 128 are different, the ENP 100 should be temporarily deformed so as to substantially match the second curvature 128 of ENP 100 to the first curvature 126 of the needle 116, thus permitting the ENP 100 to engage the needle 116.

More specifically, for the exemplary embodiment shown in FIG. 1, the internal channel 108 is structured and arranged to receive the needle 116 when the flexible body 102 is deformed so as to straighten the internal channel 108, and frictionally bind against the needle 116 when the flexible body 102 is released and attempts to return to the initial first curved state 112.

In general, the length 110 of the ENP 100, and more specifically the internal channel 108 is longer then the length 130 of the needle 116. As such, the entire shaft 118 of the needle 116 may be disposed within the internal channel 108 and thereby protected from the elements and/or contact until such time as use of the needle 116 is desired.

It is also to be appreciated that the internal channel 108 has a diameter that is greater than the outside diameter of the needle 116, such that when the flexible body 102 is deformed to straighten the internal channel 108, or otherwise substantially conform the second curvature 128 of ENP 100 to the first curvature 126 of the needle 116, the internal channel 108 is loose about the needle 116.

As the internal channel 108 is loose about the needle so long as force is applied to deform the flexible body 102, the likelihood of the internal channel 108 being shaved by the needle during the process of disposing the ENP 100 about the needle 116 is substantially reduced.

Additionally, the issue of tolerance in sizing as between the diameter internal channel 108 and the outside diameter of the needle 116 is effectively rendered moot. As the internal diameter of the internal channel 108 is intentionally substantially greater then the outside diameter of the needle 116, slight variations in manufacturing such as by an extrusion process will not dramatically affect the advantageous property of the ENP 100 to easily receive the needle 116 when the flexible body 102 is deformed, and frictionally bind to the needle 116 when the flexible body 102 is released.

In addition, as the internal channel 108 is oversized with respect to the outside diameter of the needle 116, a given ENP 100 may be advantageously suitable for use with a plurality of different needles. This may advantageously reduce the number of variations of ENPs 100 that need to be fabricated for use in protecting a wide range of different needles.

To summarize, for at least one embodiment provided is an ENP 100 for a needle 116 having a first curvature 126, including: a flexible body 102 having a first end 104 and a second end 106, and an internal channel 108 extending from the first end 104 towards the second end 106; the flexible body 102 formed of a resilient material structured and arranged to return to a curved state along the length 110 of the flexible body 102 according to a second curvature 128 different from the first curvature 126 of the needle 116; and the internal channel 108 structured and arranged to receive the needle when the flexible body is deformed to conform the internal channel 108 to the first curvature 126 and frictionally bind against the straight needle when the flexible body is released back to the second curvature 128.

For yet another embodiment, provided is an ENP 100 for a straight needle 116, including: a curved flexible body 102 having a first end 104 and a second end 106, and an internal channel 108 extending from the first end 104 towards the second end 106 along the curve of the flexible body 102 in an initial curved state 112; the internal channel 108 structured and arranged to receive the straight needle 116 when the flexible body 102 is deformed to straighten the internal channel 108 and frictionally bind against the straight needle 116 when the flexible body 102 is released back to the first initial curved state 112.

Having generally described the nature of the ENP 100, FIGS. 2A through 2E will now be discussed with respect to how the ENP 100 advantageously departs from traditional needle protectors and therefore also alleviates troublesome issues associated therewith.

Figure 2A:
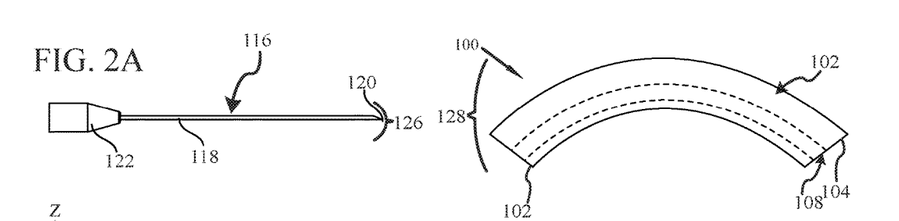
FIGS. 2A-2E illustrate a side view of the ergonomic needle protector as shown in FIG. 1 being deformed to align to a straight needle, disposed upon the straight needle and then released to frictionally grasp the straight needle in accordance with at least one embodiment of the present invention.

FIG. 2A-2E present side views of ENP 100 and needle 116 as originally shown in FIG. 1. Continuing with the exemplary embodiment of FIG. 1, the needle 116 has a first curvature of zero, such that needle 116 is appreciated to be a straight needle 116. ENP 100 as shown in FIG. 2A is shown in its initial first curved state 112. As is clearly visually apparent, the second curvature 128 of ENP 100 is quite different from the first curvature 126 of the needle 116. More simply stated, the ENP 100 is clearly curved while needle 116 is clearly straight.

The initial orientation of the internal channel 108 may also be appreciated to be quite different from the straight nature of the needle 116. In this initial condition, the ENP 100 cannot receive the needle 116.

Figure 2B:
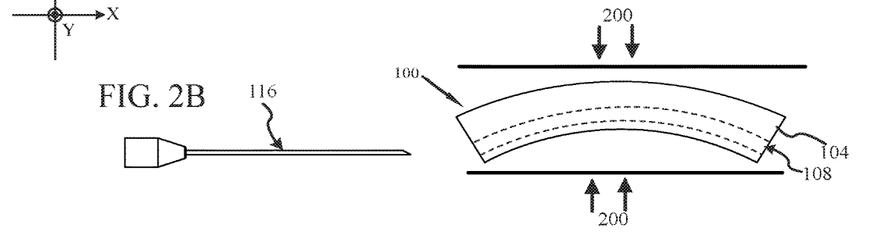

In FIG. 2B, force 200 is applied to the flexible body 102 in opposition to the second curvature 128. This force 200 may be applied by squeezing the ENP 100 by hand or with a mechanical device. Simply put, the force 200 is applied to deform the ENP 100 from its initial curved state 112 to a generally straightened state. More specifically, the force 200 is applied to deform the ENP 100 such that its second curvature 128 closely approximates the first curvature 126 of the needle 116.

Figure 2C:
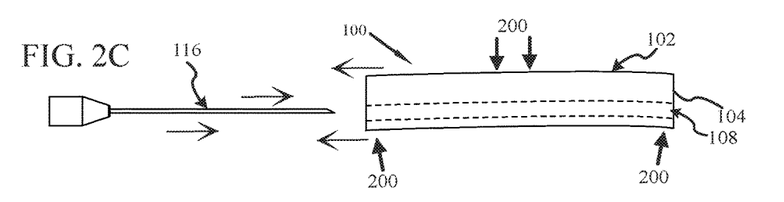
Figure 2D:
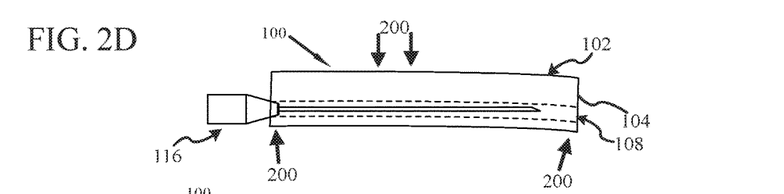

While maintaining the force 200 and thus the distortion, as shown in FIG. 2C the ENP 100 and needle 116 are fitted together. As shown in FIG. 2D the needle 116 is fully disposed within the internal channel 108 of ENP 100. With respect to both FIGS. 2C and 2D, the nature of the internal channel 108 having a diameter substantially larger than the outside diameter of the needle 116 may also be appreciated. Specifically the needle 116 is loose within the internal channel 108 of ENP 100.

Indeed ENP 100 and more specifically the internal channel 108 does not have to be perfectly distorted to match the first curvature 126 because the diameter of the internal channel 108 is so much larger then the diameter of the needle 116. In this distorted state the "slip fit" nature of the internal channel 108 about the needle 116 is such that there is effectively no frictional hold between the ENP 100 and the needle 116. This changes when force 200 is removed such that the flexible body 102 is released and it strives to return to the second curvature 128.

Figure 2E:
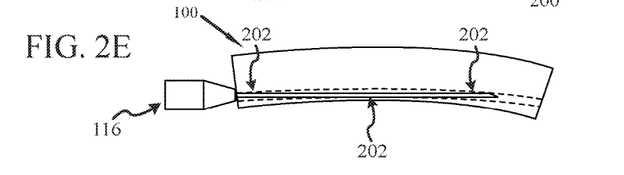

As shown in FIG. 2E, because of the presence of the needle 116 now disposed within the internal channel 108, the flexible body 102 is generally unable to return completely to the second curvature 128, however the bias to do so ensures that portions of the sidewall 202 of the internal channel 108 will now frictionally bind against the needle 116. This frictional binding is sufficient to hold the ENP 100 in place and thus protect the needle 116.

For embodiments where the internal channel 108 is closed off at the second end 106, when the deposition of ENP 100 is performed in a generally sterile environment, the needle 116 is both protected and it's sterility maintained by ENP 100. As shown in FIGS. 2A-2E the internal channel 108 has been shown as continuous through the flexible body 102 so as to visually appreciate that the portion of the flexible body extending beyond the end of the needle 116 is biasing downward and thus engaging the internal channel 108 with the end of the needle 116.

Figure 3A:
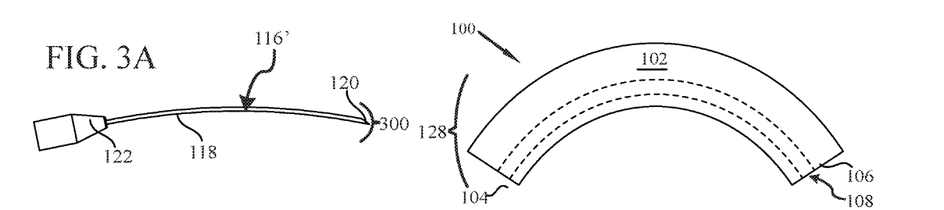
FIGS. 3A-3E illustrate a side view of the ergonomic needle protector as shown in FIG. 1 being deformed to align to a curved needle, disposed upon the curved needle and then released to frictionally grasp the curved needle in accordance with at least one embodiment of the present invention.

As noted above, ENP 100 is also advantageous for situations where the needle 116 is not a straight needle. For yet another embodiment, FIGS. 3A-3E present side views of ENP 100 and needle 116'. For this exemplary embodiment, needle 116' is not straight, but rather has a first curvature corresponding to a portion of a circle. More specifically, as shown needle 116' has a first curvature 300 of about 14°, and is a curved needle. ENP 100 as shown in FIG. 3A is shown in its initial first curved state 112. On the same drawing scale for about 14° of needle 116', ENP 100 has a second curvature of about 65°. As is clearly visually apparent, the second curvature 128 of ENP 100 is quite different from the first curvature 126 of the needle 116.

The initial orientation of the internal channel 108 may also be appreciated to be quite different from the nature of the needle 116'. In this initial condition, the ENP 100 cannot receive the needle 116'.

Figure 3B:
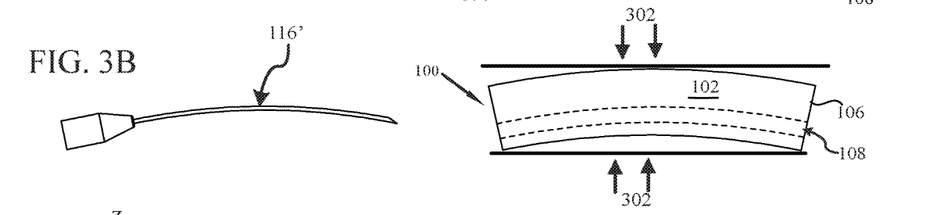

In FIG. 3B, force 302 is applied to the flexible body 102 in opposition to the second curvature 128. This force 302 may be applied by squeezing the ENP 100 by hand or with a mechanical device. More specifically, the force 302 is applied to deform the ENP 100 such that its second curvature 128 closely approximates the first curvature 300 of the needle 116'.

Figure 3C:
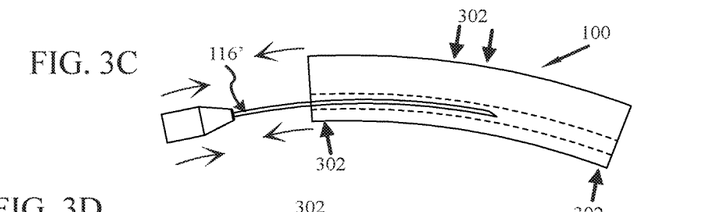
Figure 3D:
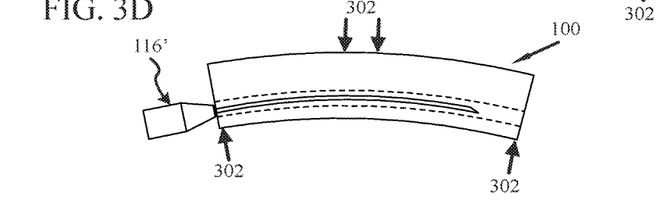

While maintaining the force 302 and thus the distortion, as shown in FIG. 3C the ENP 100 and needle 116' are fitted together. As shown in FIG. 3D the needle 116' is fully disposed within the internal channel 108 of ENP 100. With respect to both FIGS. 3C and 3D, the nature of the internal channel 108 having a diameter substantially larger than the outside diameter of the needle 116' may also be appreciated. Specifically the needle 116' is loose within the internal channel 108 of ENP 100.

Indeed ENP 100 and more specifically the internal channel 108 does not have to be perfectly distorted to match the first curvature 300 because the diameter of the internal channel 108 is so much larger then the diameter of the needle 116'. In this distorted state the "slip fit" nature of the internal channel 108 about the needle 116' is such that there is effectively no frictional hold between the ENP 100 and the needle 116'. This changes when force 302 is removed such that the flexible body 102 is released and it strives to return to the second curvature 128.

Figure 3E:
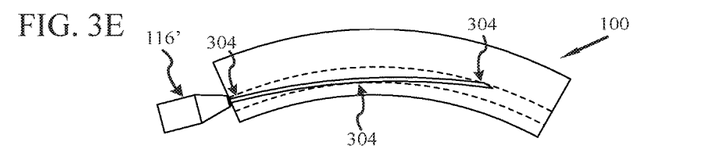

As shown in FIG. 3E, because of the presence of the needle 116' now disposed within the internal channel 108, the flexible body 102 is generally unable to return completely to the second curvature 128, however the bias to do so ensures that portions of the sidewall 304 of the internal channel 108 will now frictionally bind against the needle 116'. This frictional binding is sufficient to hold the ENP 100 in place and thus protect the needle 116'.

As shown in FIGS. 2A-2E & 3A-3E the internal channel 108 has been shown as continuous through the flexible body 102 so as to visually appreciate that the portion of the flexible body extending beyond the end of the needle 116/116' is biasing downward and thus engaging the internal channel 108 with the end of the needle 116/116'.

With respect to both straight needles 116 and curved needles 116', for embodiments where the internal channel 108 is closed off at the second end 106, when the deposition of ENP 100 is performed in a generally sterile environment, the needle 116/116' is both protected and it's sterility maintained by ENP 100. Further, with respect to the above examples presented in FIGS. 2A-2E & 3A-3E, it will be appreciated that the same ENP 100 is being employed to protect two distinctly different needles—straight needle 116 and curved needle 116', thus further demonstrating the advantageous ability of ENP 100 to protect a wide range of different needles.

It should be understood and appreciated that the degree of frictional binding achieved is a factor based on several elements, including but not limited to, how different the second curvature 128 of ENP 100 is from the first curvature 128/300 of the needle 116/116', the degree of springiness selected for the bias nature of the material forming the flexible body 102, the frictional grab quality of the material comprising the flexible body 102, and combinations thereof. For at least one embodiment, an additional material having a tacky property may be applied to the internal channel 108. For at least one other alternative embodiment, the sidewall of the internal channel 108 is texturized, or roughened.

For at least one embodiment, during the fabrication of ENP 100, one side may be heated or chemically treated so as to cause the material to contract and thus provide both the curved nature, i.e. the second curvature 128, and the bias to return to the second curvature 128 when deformed. For yet another embodiment, a curved spring element may be disposed within the flexible body and generally parallel to the internal channel 108 so as to provide or further enhance both the curved nature, i.e. the second curvature 128, and the bias to return to the second curvature 128.

Figure 4A:
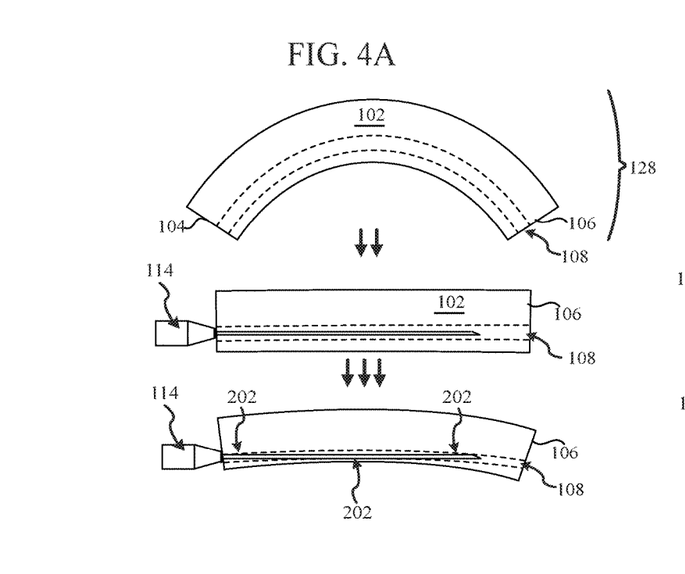
FIG. 4A presents a side view of an ergonomic needle protector having an initial curvature corresponding to a portion of a circle in accordance with at least one embodiment.
Figure 4B:
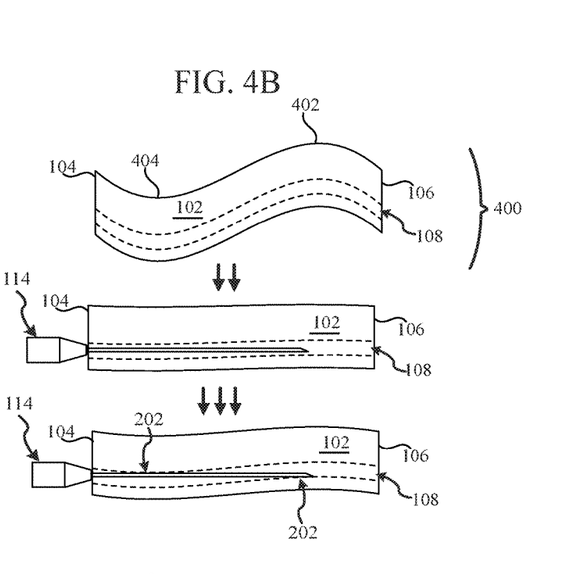
FIG. 4B presents a side view of an ergonomic needle protector having an initial curvature corresponding to a portion of a wave in accordance with at least one embodiment.
Figure 4C:
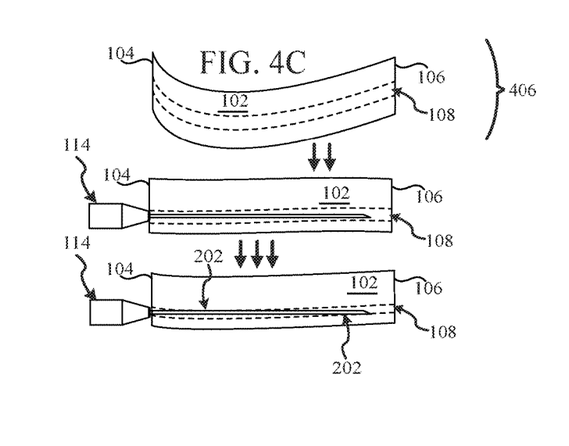
FIG. 4C presents a side view of an ergonomic needle protector having an initial curvature corresponding to a portion of ellipsis or parabola in accordance with at least one embodiment.

FIGS. 4A, 4B and 4C further illustrate various embodiments of ENP 100 each having a different initial state, e.g.

second curvature as noted above. More specifically, in FIG. 4A, the flexible body 102 corresponds to that shown in FIGS. 1 and 2A-2E wherein the second curvature 128 corresponds to a portion of a circle. In FIG. 4B the flexible body 102 has a second curvature 400 that corresponds to a wave form having at least peak and one trough one and 404. In FIG. 4C the flexible body 102 has a second curvature 406 corresponds to a portion of an ellipsis, or parabola.

With respect to FIG. 4B and the wave form embodiment, it should be understood and appreciated that the wave form may be about half of a wave period as shown, about a full wave period, or multiple portions of the wave period. It should also be understood and appreciated that the wave form may change over the length of the flexible body 102.

For ease of illustration and discussion, for each of these depicted variations, the first curvature 126 of the needle 116 is understood to be effectively zero such that the needle 116 is a straight needle. As shown, for each embodiment variation, the flexible body 102 can be distorted such that the internal channel 108 is effectively straightened, thus substantially matching the first curvature 126 of the needle 116 so as to receive the needle 116 without frictional hindrance. In other words, the ENP 100 and needle 116 may be easily slipped together such that the ENP 100 is disposed entirely about the needle 116.

When each flexible body 102 is released, the initial bias strives to return the flexible body 102 to the second curvature and a frictional hold between the internal channel 108 and the needle 116 is achieved sufficient to keep the ENP 100 in place and safeguard the needle.

Figure 5A:
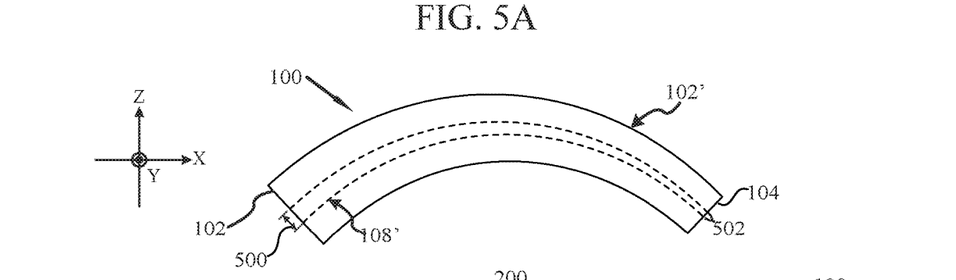
FIG. 5A-5C present side views of a tapered ergonomic needle protector in accordance with at least one embodiment.
Figure 5B:
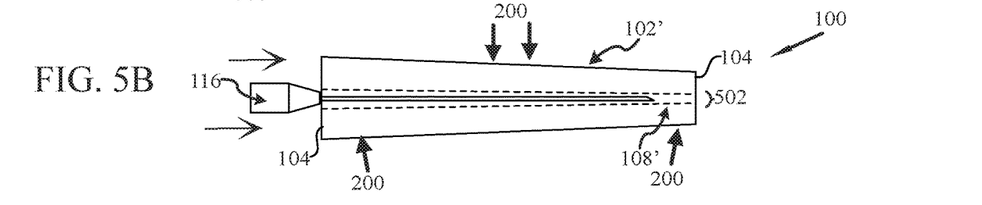
Figure 5C:
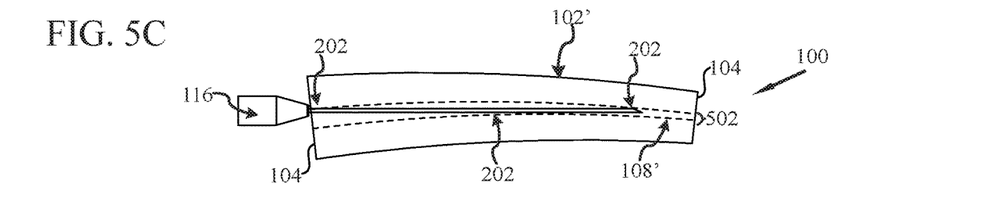

FIGS. 5A-5C present yet another embodiment for ENP 100. More specifically, as shown in FIG. 5A, for at least one embodiment the internal channel 108' tapers from a first cross section 500 adjacent to the first end 104 to a second cross section 502 adjacent to the second end 106, the second cross section 502 being smaller than the first cross section 500. In addition, for at least one embodiment the flexible body 102' is also tapered as shown. Of course it is to be understood and appreciated that the tapering of the internal channel 108' and the tapering of the flexible body 102' need not occur in the same embodiment as shown.

As discussed with respect to FIGS. 2A-2E and 3A-3E above, as shown in FIG. 5B, force 200 is applied to distort the second curvature 128 of the flexible body 102' and the needle 116 is moved into the internal channel 108'. Again, it will be appreciated that as the internal diameter of the internal channel 108' is larger then the outside diameter of the needle 116, this is a loose slip fitting between the needle 116 and ENP 100.

As noted and discussed above, when the force is removed, the bias of the flexible body 102' desiring to return to the second curved state 128 is such that portions of the internal sidewall 202 frictionally bind against the needle 116 with sufficient force as to keep the ENP 100 disposed about the needle 116 until such time as sufficient force is applied to ENP 100 to again cause distortion and release the frictional hold.

Figure 6:
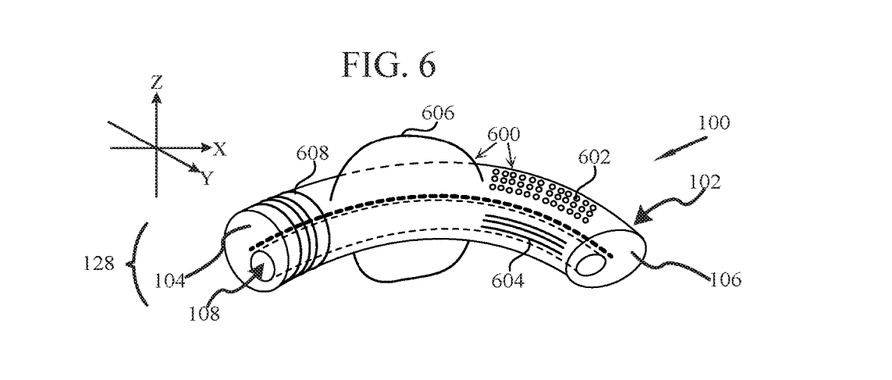
FIG. 6 presents a perspective view of an ergonomic needle protector having optional graspers in accordance with at least one environment.

FIG. 6 shows yet another embodiment for ENP 100, this time with graspers 600 structured and arranged to facilitate a user grasping the flexible body. In varying embodiment these graspers 600 may be, but are not strictly limited to, surface texture 602, ribs 604, butterfly tabs 606, rings 608, or other structures. Although these have been shown in combination for ease of illustration and discussion, varying embodiments may employ graspers 600 in combinations or alone.

Moreover, various embodiments of ENP 100 may be selected and/or provided to not only protect a needle 116, but also to assist the end user with options to easily remove the ENP 100 and enable use of the needle 116. Indeed, for at least one embodiment, ENP 100 is provided as a component of an infusion set with an ergonomic needle protector.

More specifically, the infusion set consists of a needle 116 having a base attached to infusion tubing, the needle having a shaft 118 and a sharpened tip 120, the shaft 118 having a first curvature 126; and an ENP 100 having a flexible body 102 having a first end 104 and a second end 106, and an internal channel 108 extending from the first end 104 towards the second end 108, the flexible body 102 formed of a resilient material biased to return to a second curvature 128 different from the first curvature 126, the internal channel 108 disposed about the shaft 118 and sharpened tip 120 of the needle 116, the bias of the flexible body 102 providing a friction hold against the shaft 118 of the needle 116. When use of the infusion system is desired, the user or administrator may remove the ENP 100 by pulling it off.

Figure 7:
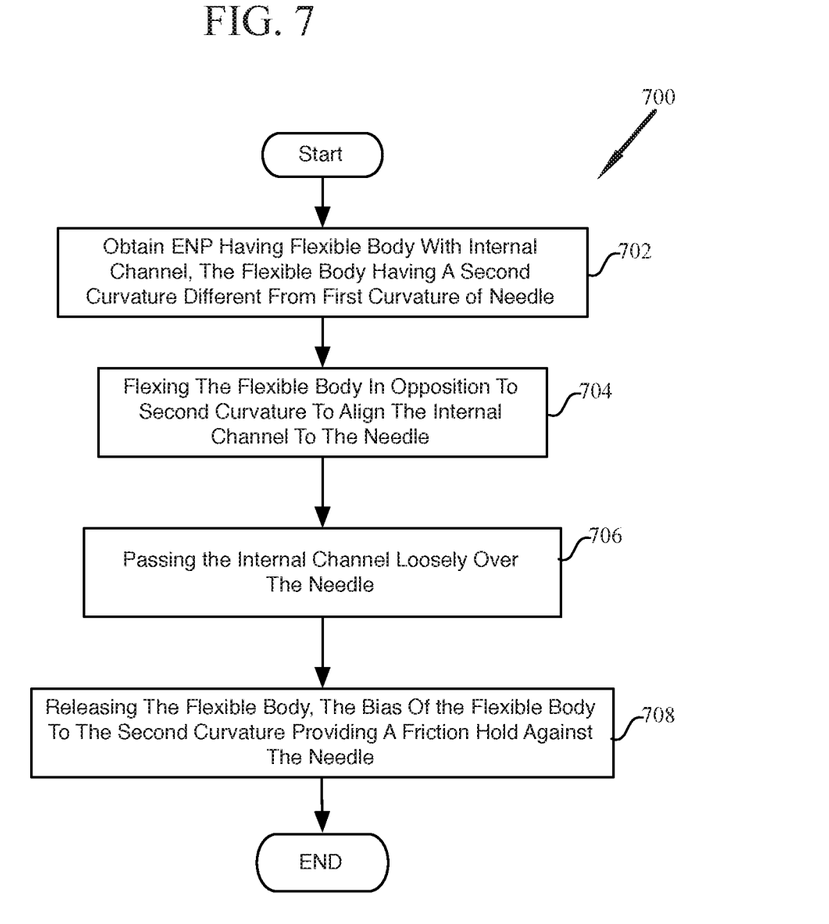
FIG. 7 presents a method of using an ergonomic needle protector in accordance with at least one embodiment.

Having described embodiments for ENP 100, another embodiment relating to at least one method 700 of using the ENP 100 will now be discussed with respect to the above illustrations and the flow diagram presented in FIG. 7. It will be understood and appreciated that the described method 700 need not be performed in the order in which it is herein described, but that this is merely exemplary of one method 700 of using ENP 100.

In general, the method 700 of use commences with obtaining an ENP 100 having a flexible body 102 having a first end 104 and a second end 106, and an internal channel 108 extending from the first end 104 towards the second end 106, the flexible body 102 formed of a resilient material biased to return to a second curvature 128 different from the first curvature 126 of the needle 116, block 702.

Method 700 proceeds with flexing the flexible body 102 of ENP 100 in opposition to the second curvature 128 to align the internal channel 108 to the needle 116, block 704. Method 700 then continues with passing the internal channel 108 loosely over the needle 116, block 706. Finally, to secure the ENP 100 as disposed upon the needle, method 700 concludes by releasing the flexible body 102, the bias of the flexible body 102 to return to the second curvature 128 providing a friction hold against the needle 116, block 708.

Changes may be made in the above methods, systems and structures without departing from the scope hereof. It should thus be noted that the matter contained in the above description and/or shown in the accompanying drawings should be interpreted as illustrative and not in a limiting sense. Indeed many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. An ergonomic needle protector for a needle having a first curvature, comprising:

a flexible body having a first end and a second end, and an internal channel extending from the first end towards the second end;

the flexible body formed of a resilient material structured and arranged to return to a curved state along the length of the flexible body according to a second curvature different from the first curvature of the needle; and the internal channel structured and arranged to receive the needle when the flexible body is deformed to conform the internal channel to the first curvature and frictionally bind against the needle having the first curvature when the flexible body is released back to the second curvature.

2. The ergonomic needle protector of claim 1, wherein the first curvature is effectively a straight line, such that the needle is a straight needle.

3. The ergonomic needle protector of claim 1, wherein the first curvature is a section of a circle, such that the needle is a curved needle.

4. The ergonomic needle protector of claim 1, wherein the first curvature is a section of an ellipse, such that the needle is a curved needle.

5. The ergonomic needle protector of claim 1, wherein the flexible body has a generally round cross section.

6. The ergonomic needle protector of claim 1, wherein the internal channel has a generally round cross section.

7. The ergonomic needle protector of claim 1, wherein the internal channel is offset from a longitudinal centerline of the flexible body.

8. The ergonomic needle protector of claim 1, wherein the internal channel has a diameter greater than an outside diameter of the needle such that when the flexible body is deformed to approximate the first curvature the internal channel is loose about the needle.

9. The ergonomic needle protector of claim 1, wherein the second curvature of the flexible body is a section of a wave form with at least one peak and one trough.

10. The ergonomic needle protector of claim 1, wherein the second curvature of the flexible body is a section of a circle.

11. The ergonomic needle protector of claim 1, wherein the second curvature of the flexible body is a section of an ellipse.

12. The ergonomic needle protector of claim 1, wherein the internal channel is open to both the first end and the second end.

13. The ergonomic needle protector of claim 1, wherein the internal channel is open to the first end and closed adjacent to the second end.

14. The ergonomic needle protector of claim 1, wherein the internal channel tapers from a first cross section area adjacent to the first end to a second cross section proximate to the second end, the second cross section area less than the first cross section area.

15. The ergonomic needle protector of claim 1, wherein the flexible body tapers from the first end towards the second end.

16. The ergonomic needle protector of claim 1, wherein the flexible body provides at least one or more graspers structured and arranged to facilitate a user grasping the flexible body and remove the flexible body from the needle.

17. The ergonomic needle protector of claim 16, wherein the graspers are selected from the group consisting of: surface texture, ribs, butterfly tabs, and rings.

18. An ergonomic needle protector for a straight needle, comprising:
a curved flexible body having a first end and a second end, and an internal channel extending from the first end towards the second end along the curve of the flexible body in an initial curved state;
the internal channel structured and arranged to receive the straight needle when the flexible body is deformed to straighten the internal channel and frictionally bind against the straight needle when the flexible body is released back to the initial curved state.

19. The ergonomic needle protector of claim 18, wherein the flexible body is formed of a resilient material structured and arranged to return to a first curved state along the length of the flexible body.

20. The ergonomic needle protector of claim 18, wherein the flexible body has a generally round cross section.

21. The ergonomic needle protector of claim 18, wherein the internal channel has a generally round cross section.

22. The ergonomic needle protector of claim 18, wherein the internal channel is offset from a longitudinal centerline of the flexible body.

23. The ergonomic needle protector of claim 18, wherein the internal channel has a diameter greater than an outside diameter of the straight needle such that when the flexible body is deformed to straighten the internal channel the flexible body is loose about the straight needle.

24. The ergonomic needle protector of claim 18, wherein the curve of the flexible body is a section of a circle.

25. The ergonomic needle protector of claim 18, wherein the curve of the flexible body is a section of an ellipse.

26. The ergonomic needle protector of claim 18, wherein the internal channel is open to both the first end and the second end.

27. The ergonomic needle protector of claim 18, wherein the internal channel is open to the first end and closed adjacent to the second end.

28. The ergonomic needle protector of claim 18, wherein the internal channel tapers from a first cross section area adjacent to the first end to a second cross section proximate to the second end, the second cross section area less than the first cross section area.

29. The ergonomic needle protector of claim 18, wherein the flexible body tapers from the first end towards the second end.

30. The ergonomic needle protector of claim 18, wherein the flexible body provides at least one or more graspers structured and arranged to facilitate a user grasping the flexible body and remove the flexible body from the needle.

31. The ergonomic needle protector of claim 30, wherein the graspers are selected from the group consisting of: surface texture, ribs, butterfly tabs, and rings.

32. An infusion set with ergonomic needle protector, comprising:
a needle having a base attached to an infusion tubing, the needle having a shaft and a sharpened tip, the shaft having a first curvature; and
an ergonomic needle protector having a flexible body having a first end and a second end, and an internal channel extending from the first end towards the second end, the flexible body formed of a resilient material biased to return to a second curvature different from the first curvature, the internal channel disposed about the shaft and sharpened tip of the needle, the bias of the flexible body providing a friction hold against the shaft, wherein the ergonomic needle protector is removed by pulling the flexible body off.

33. The infusion set with ergonomic needle protector of claim 32, wherein the first curvature is effectively a straight line, such that the needle is a straight needle.

34. The infusion set with ergonomic needle protector of claim 32, wherein the first curvature is a section of a circle, such that the needle is a curved needle.

35. The infusion set with ergonomic needle protector of claim 32, wherein the first curvature is a section of an ellipse, such that the needle is a curved needle.

36. The infusion set with ergonomic needle protector of claim 32, wherein the flexible body has a generally round cross section.

37. The infusion set with ergonomic needle protector of claim 32, wherein the internal channel has a generally round cross section.

38. The infusion set with ergonomic needle protector of claim 32, wherein the pulling off includes deforming the flexible body to conform the second curvature to about the first curvature to release the friction hold.

39. The infusion set with ergonomic needle protector of claim 32, wherein the flexible body has a generally round cross section.

40. The infusion set with ergonomic needle protector of claim 32, wherein the internal channel has a generally round cross section.

41. The infusion set with ergonomic needle protector of claim 32, wherein the internal channel is offset from a longitudinal centerline of the flexible body.

42. The infusion set with ergonomic needle protector of claim 32, wherein the internal channel has an internal diameter greater than an outside diameter of the needle such that when the flexible body is deformed to approximate the first curvature the internal channel is loose about the needle.

43. The infusion set with ergonomic needle protector of claim 32, wherein the second curvature of the flexible body is selected from the group consisting of: a section of a circle, a section of an ellipse, and a wave.

44. A method of protecting a needle having a first curvature with an ergonomic needle protector, comprising:
    obtaining an ergonomic needle protector having a flexible body having a first end and a second end, and an internal channel extending from the first end towards the second end, the flexible body formed of a resilient material biased to return to a second curvature different from the first curvature;
    flexing the flexible body in opposition to second curvature to align the internal channel to the needle;
    passing the internal channel loosely over the needle; and
    releasing the flexible body, the bias of the flexible body to the second curvature providing a friction hold against the needle.

45. The method of claim 44, wherein the first curvature is effectively a straight line, such that the needle is a straight needle.

46. The method of claim 44, wherein the first curvature is a section of a circle, such that the needle is a curved needle.

47. The method of claim 44, wherein the first curvature is a section of an ellipse, such that the needle is a curved needle.

48. The method of claim 44, wherein the flexible body has a generally round cross section.

49. The method of claim 44, wherein the internal channel has a generally round cross section.

50. The method of claim 44, wherein the internal channel is offset from a longitudinal centerline of the flexible body.

51. The method of claim 44, wherein the second curvature of the flexible body is selected from the group consisting of: a section of a circle, a section of an ellipse, and a wave.

52. The method of claim 44, wherein the internal channel is open to both the first end and the second end.

53. The method of claim 44, wherein the internal channel is open to the first end and closed adjacent to the second end.

54. The method of claim 44, wherein the internal channel tapers from a first cross section area adjacent to the first end to a second cross section proximate to the second end, the second cross section area less than the first cross section area.

55. The method of claim 44, wherein the flexible body tapers from the first end towards the second end.

* * * * *